(12) United States Patent
Ozawa et al.

(10) Patent No.: US 8,665,327 B2
(45) Date of Patent: Mar. 4, 2014

(54) ENDOSCOPE SYSTEM WITH COLOR CORRECTION INFORMATION

(75) Inventors: Satoshi Ozawa, Kanagawa (JP); Takayuki Iida, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 561 days.

(21) Appl. No.: 12/888,771

(22) Filed: Sep. 23, 2010

(65) Prior Publication Data
US 2011/0069161 A1    Mar. 24, 2011

(30) Foreign Application Priority Data
Sep. 24, 2009    (JP) ................. P2009-219245

(51) Int. Cl.
*A61B 1/04*    (2006.01)

(52) U.S. Cl.
USPC .......................................... 348/68

(58) Field of Classification Search
USPC .......................................... 348/68
See application file for complete search history.

(56) References Cited

U.S. PATENT DOCUMENTS

| | | | |
|---|---|---|---|
| 4,827,908 A | 5/1989 | Matsuo | |
| 6,320,331 B1 | 11/2001 | Iida et al. | |
| 2002/0016620 A1* | 2/2002 | Tsujita | 607/88 |
| 2003/0035301 A1 | 2/2003 | Gardiner et al. | |
| 2006/0235277 A1 | 10/2006 | Ohkubo et al. | |
| 2007/0211274 A1* | 9/2007 | Donomae | 358/1.9 |
| 2008/0089089 A1 | 4/2008 | Hama et al. | |
| 2008/0232131 A1 | 9/2008 | Suda | |
| 2009/0054957 A1* | 2/2009 | Shanbaky | 607/89 |
| 2010/0254153 A1 | 10/2010 | Hama et al. | |

FOREIGN PATENT DOCUMENTS

| | | |
|---|---|---|
| EP | 1 795 798 A1 | 6/2007 |
| JP | 10-276975 | 10/1998 |
| JP | 2000-342533 A | 12/2000 |
| JP | A-2004-121549 | 4/2004 |
| JP | A-2006-296656 | 11/2006 |
| JP | A-2008-258177 | 10/2008 |
| JP | A-2008-264514 | 11/2008 |

OTHER PUBLICATIONS

European Search Report dated Dec. 23, 2010.
Japanese Office Action dated Mar. 19, 2013 with a partial English translation.

* cited by examiner

*Primary Examiner* — Richard Torrente
(74) *Attorney, Agent, or Firm* — McGinn IP Law Group, PLLC

(57) ABSTRACT

Provided is an endoscope system including an endoscope which includes an illumination optical system having a fluorescent substance and an imaging optical system having an imaging element; and a control device which is connected to the endoscope. The control device includes a light source unit having a semiconductor light emitting element generating excitation light used to excite the fluorescent substance, a storage section storing predetermined color correction information, and an image processing section creating captured image data by performing a calculation process on an image signal output from the imaging element on the basis of the color correction information. At least one of optical characteristics of the fluorescent substance and the semiconductor light emitting element is detected, and the color correction information stored in the storage section is corrected on the basis of the detected optical characteristic.

8 Claims, 11 Drawing Sheets

ENDOSCOPE SYSTEM WITH COLOR CORRECTION INFORMATION

The present application claims priority from Japanese Patent Application No. 2009-219245 filed on Sep. 24, 2009, the entire content of which is incorporated herein by reference.

BACKGROUND OF INVENTION

1. Field of the Invention

The present invention relates to an endoscope system.

2. Description of the Related Art

For example, JP-A-2000-342533 discloses an endoscope system including an endoscope which has an imaging element emitting illumination light from a front end of an endoscope insertion unit and capturing an image of an observation area, and a control device which supplies the illumination light to the endoscope while being connected to the endoscope, and performs a calculation process on an imaging signal from the imaging element. In addition, recently, a technology of using a combination of a fluorescent substance and laser light as the illumination light of the endoscope has been put to practical use.

In such an endoscope system, in order to accurately examine an affected portion, a chromacity adjustment process is performed by correcting chromacity of a captured image to be the correct chromacity on the basis of a predetermined chromacity correction table. However, there is an individual difference in an optical characteristic of each endoscope and an optical characteristic of a control device to which the endoscope is connected. In addition, even when the uniform correction of the image signal output from the endoscope is attempted by the control device, it is difficult to perform the correction to be the correct chromacity at all times. Particularly, in the case of the illumination device obtained by combining the fluorescent substance with the laser light source, since the tone of the final observation image is determined by the delicate relationship of a difference in the light emission characteristic caused by the individual differences of the fluorescent substance or a difference in the light emission wavelength caused by the individual differences of the light source, when the endoscope connected to the control device is exchanged with another one, the tone of the captured image may be changed for each endoscope.

In addition, even when the correct chromacity adjustment is performed during the manufacture of the endoscope or the control device, the optical characteristic of the laser light source or the fluorescent substance may be changed over time in some cases. Generally, in the semiconductor light emitting element, there arises a variation in the optical characteristic such as a decrease in the light output in accordance with the time elapsed from the start of usage. For this reason, in the case where maintenance such as an exchange of a light source element is periodically performed, the operation needs to be performed under conditions where external light or temperature is managed. In addition, a device such as a reference color sample necessary for adjustment needs to be accommodated. Due to such inconvenience, in many cases, the maintenance is not performed by a user, but performed in the maker's factory after being transported thereto.

SUMMARY OF INVENTION

An object of the present invention is to provide an endoscope system capable of simplifying a maintenance operation performed by a user to check a variation in the tone of a captured image caused by a variation over time or the like when using an endoscope including an illumination optical system having a laser light source and a fluorescent substance and an imaging optical system having an imaging element.

The present invention has the following configuration.

Provided is an endoscope system including an endoscope which includes an illumination optical system having a fluorescent substance and an imaging optical system having an imaging element; and a control device which is connected to the endoscope, the control device including a light source unit having a semiconductor light emitting element generating excitation light used to excite the fluorescent substance, a storage section storing predetermined color correction information, and an image processing section creating captured image data by performing a calculation process on an image signal output from the imaging element on the basis of the color correction information, the endoscope system including: an optical characteristic detecting means for detecting at least one of optical characteristics of the fluorescent substance and the semiconductor light emitting element; and a color correction information correcting means for correcting the color correction information stored in the storage section on the basis of the optical characteristic detected by the optical characteristic detecting means.

It is possible to simplify a maintenance operation performed by a user to correct the color correction information in the event of a variation in the tone of the captured image caused by a variation over time or the like. Accordingly, it is possible to accurately perform the color correction on the captured image of the endoscope at all times, and to reliably maintain the high diagnosis precision of the endoscope.

DESCRIPTION OF EXEMPLARY EMBODIMENTS

Hereinafter, an embodiment of the invention will be described with reference to the accompanying drawings.

Figure 1:
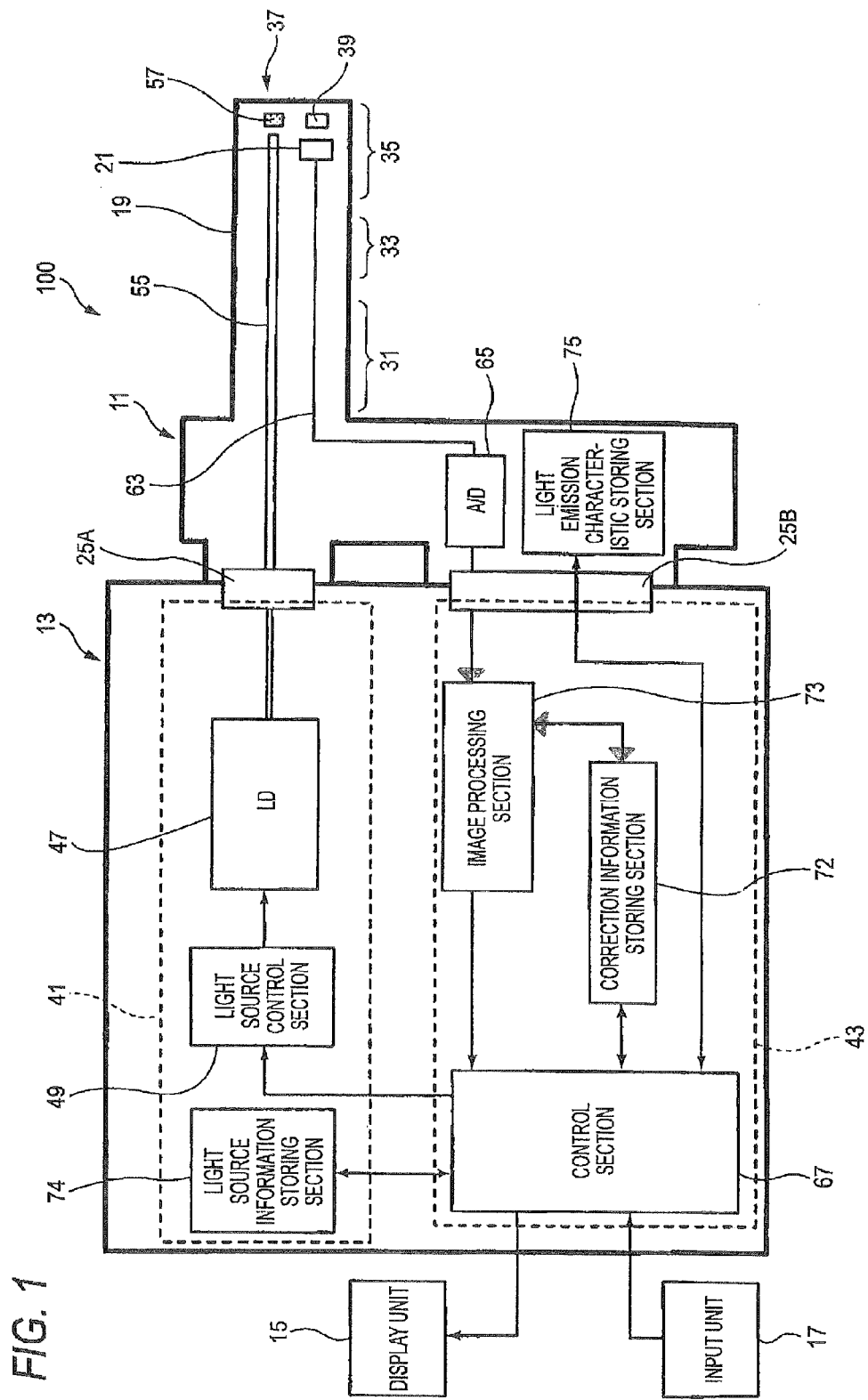
FIG. 1 is a diagram illustrating an embodiment of the invention, and a block diagram showing a configuration of an endoscope system.
Figure 2:
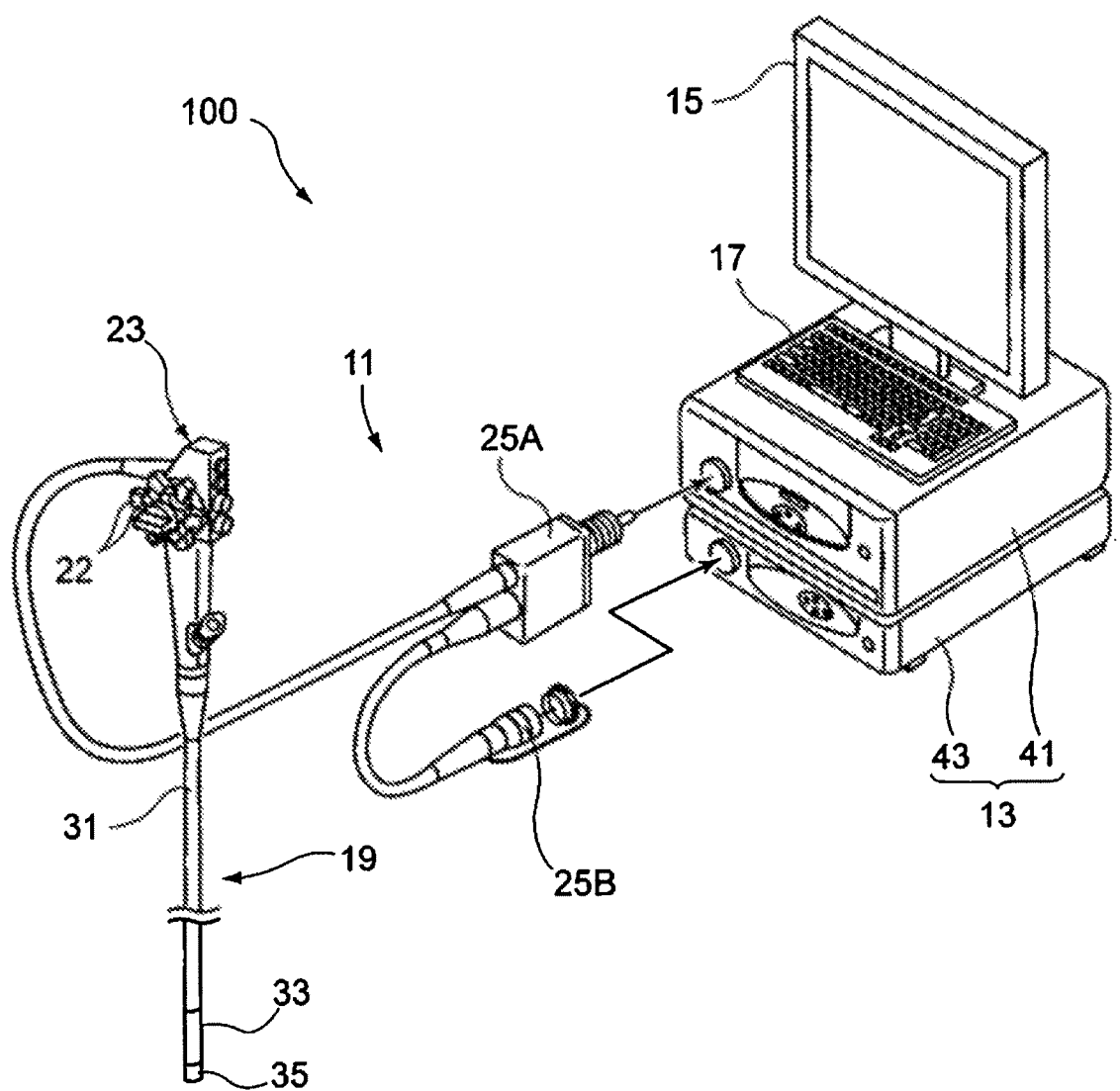
FIG. 2 is a perspective view showing a detailed example of an external appearance of the endoscope system shown in FIG. 1.

FIG. 1 is a diagram illustrating an embodiment of the invention, and is a conceptual block diagram of an endoscope system. FIG. 2 is an external view of an example of the endoscope system shown in FIG. 1.

As shown in FIGS. 1 and 2, an endoscope system 100 includes an endoscope 11, and a control device 13 to which the endoscope 11 is connected. The control device 13 is connected to a display unit 15 which displays image information or the like, and an input unit 17 which receives an input operation. The endoscope 11 is an electronic endoscope which includes an illumination optical system emitting an illumination light from a front end of an endoscope insertion unit 19 and an imaging optical system including an imaging element 21 (refer to FIG. 1) configured to image an observation area.

In addition, the endoscope 11 includes the endoscope insertion unit 19 which is inserted into a test object, an operation unit 23 (refer to FIG. 2) which is used for an operation of curving the front end of the endoscope insertion unit 19 or an observation operation, and connectors 25A and 25B which are used to attachably/detachably connect the endoscope 11 to the control device 13. In addition, although not shown in the drawings, the inside of the operation unit 23 and the endoscope insertion unit 19 is provided with various channels such as a clamp channel used for inserting a tissue pickup treatment tool or the like therethrough or an air/water feeding channel.

The endoscope insertion unit 19 includes a flexible portion 31 which has flexibility, a curved portion 33, and a front end portion (hereinafter, referred to as an endoscope front end portion) 35. As shown in FIG. 1, the endoscope front end portion 35 is provided with illumination port 37 which is used to emit a light to the observation area, and an imaging element 21 such as a CCD (Charge Coupled Device) image sensor or a CMOS (Complementary Metal-Oxide Semiconductor) image sensor which is used to acquire image information of the observation area. The light receiving surface of the imaging element 21 is provided with an object lens unit 39.

As shown in FIG. 2, the curved portion 33 is provided between the flexible portion 31 and the front end portion 35, and is adapted to be curved by a rotation operation of an angle knob 22 disposed in the operation unit 23. The curved portion 33 may be curved to an arbitrary direction and an arbitrary angle in accordance with a portion of the test object examined by the endoscope 11. The observation direction of the illumination port 37 and the imaging element 21 of the endoscope front end portion 35 may be directed to a desired observation portion. In addition, although not shown in the drawings, the illumination port 37 of the endoscope insertion unit 19 is provided with a cover glass or a lens.

The control device 13 includes a light source device 41 which generates an illumination light supplied to the illumination port 37 of the endoscope front end portion 35, and a processor 43 which performs an image process on an image signal generated from the imaging element 21, and is connected to the endoscope 11 via the connectors 25A and 25B. In addition, the processor 43 is connected to the display unit 15 and the input unit 17 which are described above. The processor 43 performs an image process on an imaging signal transmitted from the endoscope 11 on the basis of the command from the operation unit 23 of the endoscope 11 or the input unit 17 thereof, and generates and supplies a display image to the display unit 15.

In addition, a plurality of the endoscopes 11 is provided in advance, and the endoscope 11 connected to the control device 13 may be arbitrarily exchanged.

As shown in FIG. 1, the light source device 41 includes a blue laser light source (LD) 47 as a light emitting source. Specifically, the blue laser light source 47 is a laser diode which emits blue laser light having a central wavelength of 445 nm. As the blue laser light source 47, an InGaN-based laser diode of a broad area type, and an InGaNAs-based laser diode or a GaNAs-based laser diode may be used. In addition, as the above-described light source, a light emitting member such as a light emitting diode may be used. The light emission intensity of the blue laser light source (LD) 47 is controlled by the light source control section 49.

The laser light emitted from the light source 47 is input to an optical fiber by a condensing lens (not shown), and is propagated to the connector 25A. The blue laser light supplied to the connector 25A is propagated to the endoscope front end portion 35 of the endoscope 11 via an optical fiber 55.

A fluorescent substance 57 as a wavelength changing member is disposed at a position facing the light emitting end of the optical fiber 55 in the endoscope front end portion 35. The blue laser light supplied from the blue laser light source 47 via the optical fiber 55 emits fluorescence by exciting the fluorescent substance 57, and a part of the blue laser light directly passes through the fluorescent substance 57.

The optical fiber 55 is a multi-mode fiber. As an example, a thin fiber cable may be used which has a core diameter of 105 μm, a cladding diameter of 125 μm, and a diameter of Φ0.3 to 0.5 mm including a protection layer as an outer surface.

The fluorescent substance 57 includes a plurality of types of fluorescent substances which absorbs a part of energy of the blue laser light and is excited to emit light of green to yellow. As a specific example of the fluorescent substance 57, for example, a YAG-based fluorescent substance or a fluorescent substance containing BAM ($BaMgAl_{10}O_{17}$) or the like may be used. Accordingly, white (a color similar to white) illumination light is emitted from the illumination port 37 of the endoscope front end portion 35 as the result of synthesizing green to yellow excitation light as excitation light with the blue laser light not absorbed and passing through the fluorescent substance 57. Like the example of the configuration, when the semiconductor light emitting element is used as an excitation light source, it is possible to obtain white light having high light emission efficiency and high intensity. Also, it is possible to easily control the intensity of the white light.

The fluorescent substance 57 may prevent an occurrence of flickering when performing a video display or overlapping of noise as a barrier in the imaging operation due to a speckle generated by coherence of laser light. In addition, in the fluorescent substance 57, in consideration of a difference in the refractive index between the fluorescent material forming the fluorescent substance and a fixing/solidifying resin as a filling agent, it is desirable that the particles of the filling agents and the fluorescent material are formed of a material having large scattering and small absorption with respect to the infrared light. Accordingly, it is possible to improve the scattering effect without reducing the light intensity with respect to the light of red or infrared region. Also, it is not necessary to provide an optical path correcting means such as a concave lens, and it is possible to reduce the optical loss.

Figure 3:
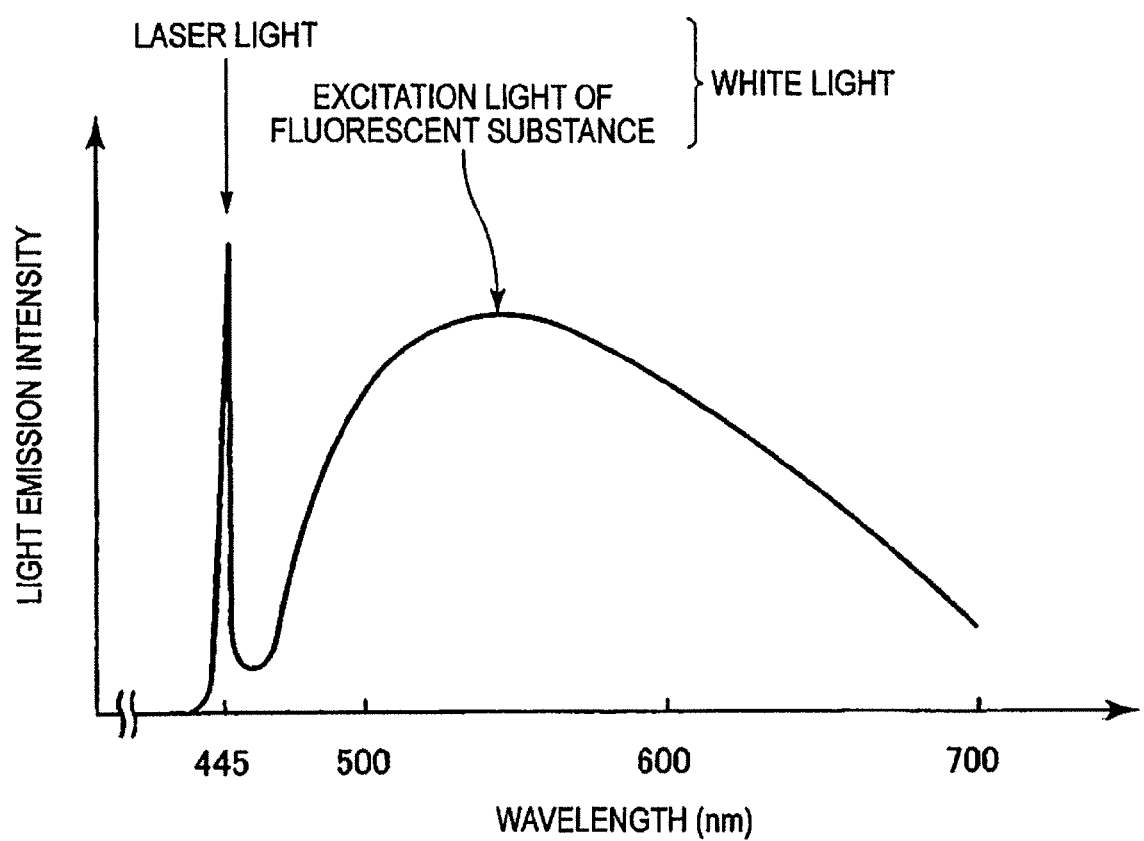
FIG. 3 is a graph showing a characteristic of the intensity distribution and wavelength of light obtained by light emitted from a fluorescent substance and light emitted from a light source.

FIG. 3 shows a detailed example of a spectrum (spectral characteristic) of illumination light emitted from the endoscope front end portion 35 of the endoscope 11 to an observation image. The blue laser light is depicted by the bright line having a central wavelength of 445 nm, and the excitation light emitted from the fluorescent substance 57 by the blue laser light has a spectroscopic distribution in which the light emission intensity substantially increases in the bandwidth of the wavelength of 450 nm to 700 nm. The above-described white light is formed by the profile of the excitation light and the blue laser light.

Here, the white light mentioned in the specification precisely includes not only all wavelength components of the visible light, but also for example, R, G, B, and the like of the light of the specific wavelength. For example, the light including the wavelength component from green to red or the light including the wavelength component from blue to green is included in the white light in a broad sense.

Returning to FIG. 1, the description thereof is continued. As described above, the white illumination light formed by the excitation light emitted from the fluorescent substance 57 and the blue laser light is emitted from the front end portion 35 of the endoscope 11 to the observation area of the test object. Then, the image of the observation area illuminated by the illumination light is formed on the light receiving surface of the imaging element 21 by the use of the object lens unit 39.

The image signal of the captured image output from the imaging element 21 after the imaging operation thereof is transmitted to an A/D converter 65 via a scope cable 63 and is converted into a digital signal. Then, the digital signal is input to the processor 43 via the connector 25B.

The processor 43 includes a control section 67 which controls the light source device 41, an image processing section 73 which is connected to the control section 67 and is described later in detail, and a correction information storing section 72. The information such as tone correction table (color correction information) necessary for a correction process of matching the captured image signal to the correct tone is created in advance, and is stored in the correction information storing section 72.

In addition, in the case where the endoscope 11 connected to the control device 13 is exchanged, information of a tone correction table is newly created in accordance with the characteristic of the fluorescent substance 57 of the endoscope 11 which is connected after the exchange, and the contents of the tone correction table are updated. For example, immediately after exchanging the endoscope 11, the control section 67 reads information from each of the light source information storing section 74 and the light emission characteristic storing section 75, and creates information necessary for the tone correction on the basis of such information. Accordingly, the contents of the tone correction table are updated.

The captured image signal output from the A/D converter 65 is input to the image processing section 73. The image processing section 73 performs an appropriate image process by converting the input digital image signal into image data, and creates desired output image information.

Figure 4:
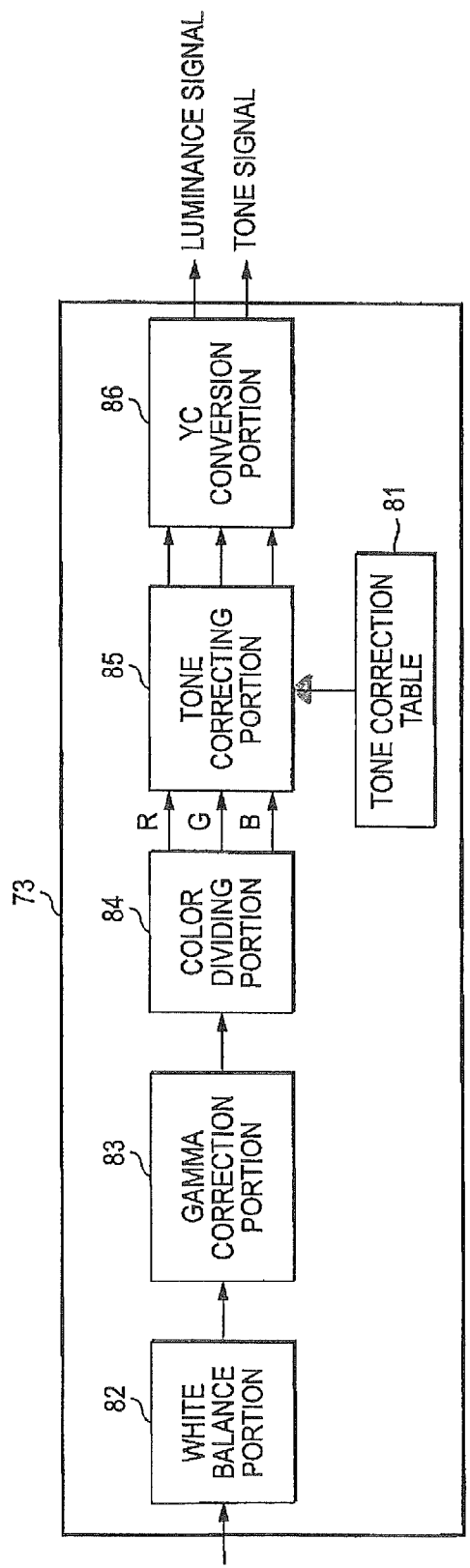
FIG. 4 is a block diagram showing a detailed configuration example of an image processing section.

FIG. 4 shows a configuration of a detailed example of the image processing section. The image processing section 73 includes a white balance portion 82, a gamma correction portion 83, a color dividing portion 84, a tone correcting portion 85, and a YC conversion portion 86. The white balance portion 82 performs a white balance adjustment on the digital image signal output from the A/D converter 65, and gives the adjusted image data to the gamma correction portion 83. The gamma correction portion 83 performs a gamma correction on the input image data. The color dividing portion 84 creates the respective image signals of R (red), G (green), and B (blue) from the image data subjected to the gamma correction, and gives the image signal to the tone correcting portion 85.

The tone correcting portion 85 reads correction data registered in a tone correction table 81 to be described later in detail, and performs a correction process on the respective image signals of R, G, and B input from the color dividing portion 84 so as to obtain an image having the correct tone. The image signal subjected to the color correction process is converted into a color video signal of a luminance signal (Y) and a color difference signal (Cb and Cr) by the YC conversion section 86.

The video signal converted into the color video signal and output from the image processing section 73 is input to the control section 67 shown in FIG. 1, and is displayed on the display unit 15 in the form of an endoscope observation image together with a variety of information by the control section 67. If necessary, the video signal is stored in a storage section configured as a memory or a storage device.

Next, the individual information of the endoscope will be described.

As shown in FIG. 1, the light emission characteristic storing section 75 is provided in the inside of the endoscope 11. The light emission characteristic storing section 75 is configured as a non-volatile memory, and stores the individual information of the endoscope 11 in advance. Specifically, the light emission spectrum information and the excitation spectrum information as the original light emission characteristic information of the fluorescent substance 57 actually provided in the endoscope 11 are stored in the light emission characteristic storing section 75. Here, the excitation spectrum information is information representing a distribution state for each wavelength involved with the energy absorption characteristic of the fluorescent substance 57 with respect to the external light supplied for the excitation. In addition, the light emission spectrum information is information representing the spectral intensity of fluorescence actually generated from the fluorescent substance 57 by the light supplied from the outside.

In fact, the light emission characteristic of the fluorescent substance 57 is measured before the use of the endoscope, and the excitation spectrum information and the light emission spectrum information obtained from the result are stored in the light emission characteristic storing section 75. Further, in addition to the measurement, the accurate characteristic information of the fluorescent substance 57 which is prepared in advance may be stored in the light emission characteristic storing section 75.

Figure 5:
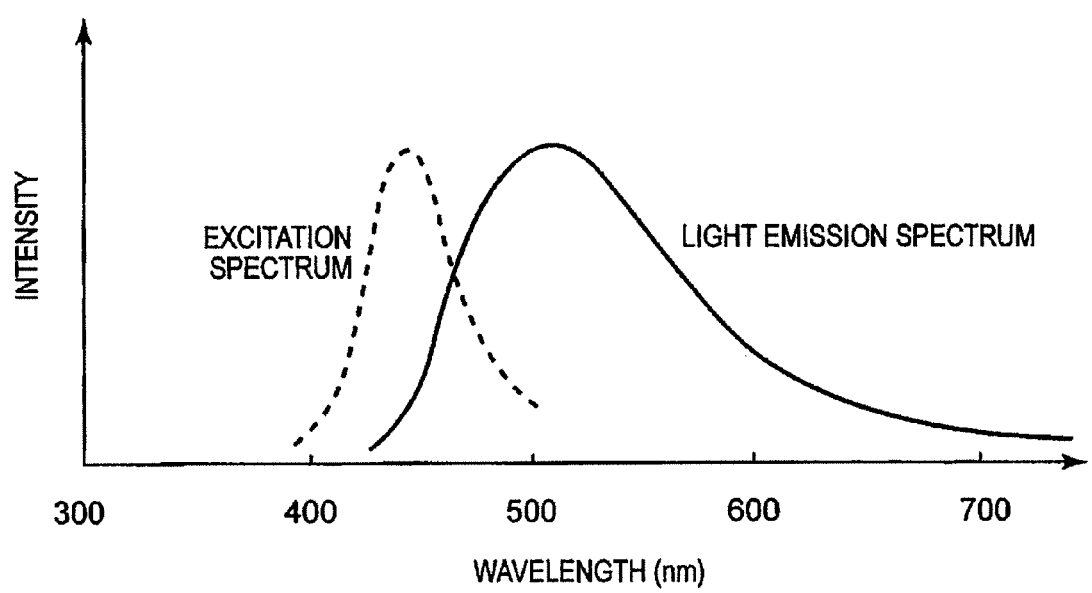
FIG. 5 is a graph showing a detailed example of an excitation spectrum and a light emission spectrum of a particular fluorescent substance.

Here, FIG. 5 shows an example of the excitation spectrum and the light emission spectrum of the particular fluorescent substance 57. In the case of the fluorescent substance 57 having the characteristic shown in FIG. 5, as seen from the curve of the excitation spectrum depicted by the dotted line, it is understood that the light within the wavelength bandwidth of about 420 to 470 nm is absorbed, and particularly, the light of the wavelength of about 445 nm is highly efficiently absorbed. The fluorescent substance 57 is excited by the absorbed excitation light, and emits fluorescence of the spectrum shown in the light emission spectrum depicted by the solid line.

In addition, the light emission intensity of the fluorescent substance 57 is changed in accordance with the magnitude of the absorbed energy. Like the excitation spectrum shown in FIG. 5, since the absorption characteristic of the excitation light of the fluorescent substance 57 is changed in accordance with the wavelength, the light emission intensity of the fluorescent substance 57 is changed in accordance with the wavelength of the light supplied from the outside.

Figure 6:
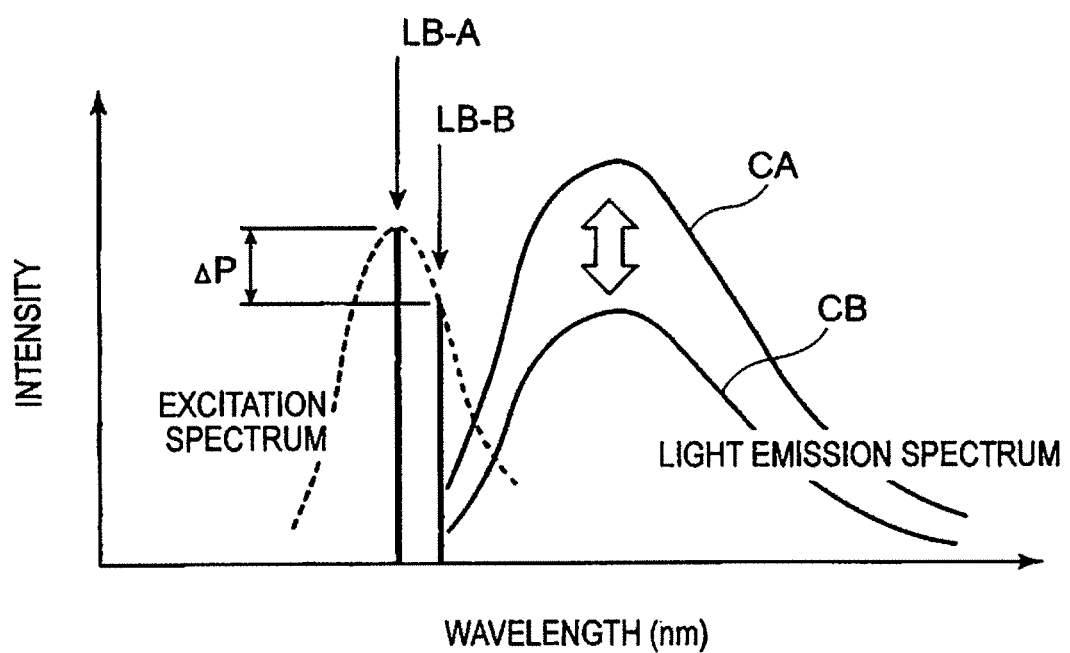
FIG. 6 is an explanatory diagram showing a variation in the light emission spectrum in the case where a light emission wavelength of a laser light source is deviated.

For example, as shown in FIG. 6, if it is assumed that the light emission wavelength of the blue laser light source 47 is deviated, in the laser beam LB-A of the stipulated wavelength of 445 nm, highly efficient absorption occurs at a wavelength at which the excitation spectrum substantially reaches the peak. However, in the laser beam of LB-B, since the light emission wavelength is deviated, the intensity of the excitation spectrum is decreased by AP. Then, in the laser beam LB-B, the light intensity is the same as that of the laser beam LB-A, and the light emission spectrum of the fluorescent substance 57 is decreased from CA to CB, which causes a relative difference in the light emission intensity of the fluorescent substance between the laser light sources LB-A and LB-B.

Regarding the excitation spectrum information and the light emission spectrum information stored in the light emission characteristic storing section 75, when the information representing the curve of each of continuous spectrums of a plurality of wavelengths is stored in a table or a numerical equation, it is possible to more highly precisely predict the spectrum of the illumination light, and to highly precisely correct the tone.

In addition, the individual information of the light source is as below.

As shown in FIG. 1, the light source device 41 includes the light source information storing section 74. The light source information storing section 74 is configured as a non-volatile memory, and stores information representing the wavelength of the laser light output from the light source as the original light source information of the light source device 41. That is, the light source information storing section 74 stores information representing the central wavelength (the wavelength having the maximum intensity) of the laser light emitted from at least the blue laser light source 47. For example, the light emission characteristic of the laser light source 47 of the light source device 41 is measured before the use (factory shipment) of the endoscope 11, and the information obtained as the result thereof is stored in the light source information storing section 74. Further, in addition to the measurement, the accurate characteristic information of the laser light source 47 which is prepared in advance may be stored in the light emission characteristic storing section 75.

Incidentally, when the endoscope system 100 is used for a long period of time, the light emission characteristic of the blue laser light source 47 of the light source device 41 or the characteristic of the fluorescent substance 57 of the endoscope 11 may be changed. Such a variation in the optical characteristic influences the tone of the illumination light emitted from the endoscope 11 to the object, and hence the imaging signal obtained from the imaging element 21 is influenced.

The contents of the tone correction table 81 used to correct the tone by the tone correcting portion 85 inside the image processing section 73 are determined on the basis of the individual information of the blue laser light source 47 stored in the light source information storing section 74 and the individual information of the fluorescent substance 57 stored in the light emission characteristic storing section 75. However, if a variation over time or a variation in the environmental condition occurs, a difference occurs between the actual characteristic of the blue laser light source 47 and the individual information stored in the light source information storing section 74, or a difference occurs between the actual characteristic of the fluorescent substance 57 and the individual information stored in the light emission characteristic storing section 75.

In the case where there is a difference between the stored individual information and the actual characteristic, the tone of the captured image cannot be correctly corrected, and the image quality is degraded.

Accordingly, in order to obtain the captured image having the correct tone by removing the influence caused by differences in the characteristics, a maintenance process is periodically performed, and the contents of the tone correction table 81 are correctly rewritten. The endoscope system 100 shown in FIG. 1 is equipped with a function of allowing a user to easily perform correction during the maintenance process.

Hereinafter, the configuration functions will be described sequentially in detail.

First, a method of correcting a difference in the characteristic of the blue laser light source 47 by using a correction endoscope will be described.

Figure 7:
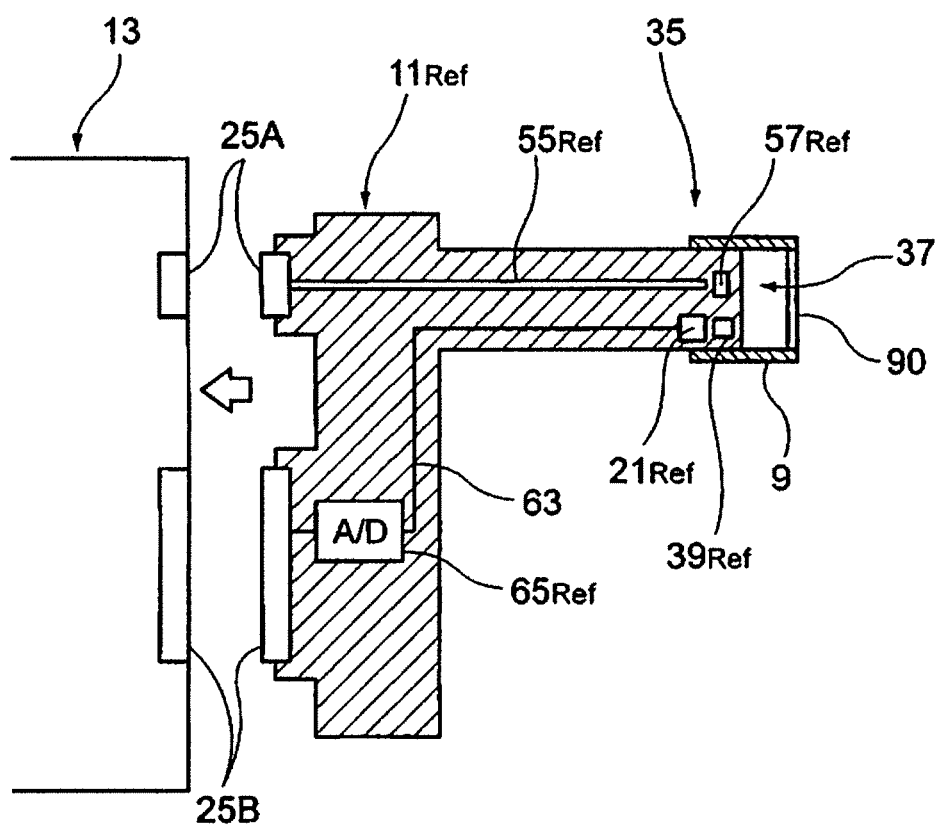
FIG. 7 is a block diagram showing a configuration of a correction endoscope used in the endoscope system shown in FIG. 1.

In order to accurately measure the characteristic of the blue laser light source 47 without the influence of a variation over time, an exclusive correction endoscope $11_{Ref}$ shown in FIG. 7 is separately prepared in advance, in addition to the endoscope 11 shown in FIG. 1. The correction endoscope $11_{Ref}$ is provided as the component of the endoscope system 100, and the user may use the correction endoscope $11_{Ref}$ if necessary. The correction endoscope $11_{Ref}$ is not used, but accommodated in a normal case. Only in the case of the maintenance, the correction endoscope $11_{Ref}$ is used while being connected to the connectors 25A and 25B of the control device 13 instead of the endoscope 11 used in a normal case.

The correction endoscope $11_{Ref}$ substantially has the same configuration as that of the endoscope 11, but only the illumination optical system and the imaging optical system are subjected to the same correction. For example, other functions such as an air/water sending function may be omitted.

The blue laser light supplied from the light source via the connector 25A while connecting the correction endoscope $11_{Ref}$ to the control device 13 is propagated to the endoscope front end portion 35 of the correction endoscope $11_{Ref}$ via an optical fiber $55_{Ref}$. A fluorescent substance $57_{Ref}$ is disposed at a position facing the light emitting end of the optical fiber $55_{Ref}$ of the endoscope front end portion 35. The blue laser light supplied from the optical fiber $55_{Ref}$ excites the fluorescent substance $57_{Ref}$ so as to emit light therefrom, and a part of the blue laser light directly passes through the fluorescent substance $57_{Ref}$. As a result, the excitation light of green to yellow generated from the fluorescent substance $57_{Ref}$ by the excitation of the blue laser light and the blue laser light passing through the fluorescent substance $57_{Ref}$ are synthesized at the illumination portion 37 of the endoscope front end portion 35, and the white illumination light is emitted therefrom.

The fluorescent substance $57_{Ref}$ is basically formed of the same material as that of the above-described fluorescent substance 57, but has an ideal characteristic which may be used as a reference. That is, the excitation spectrum or the light emission spectrum of the fluorescent substance $57_{Ref}$ is close to the characteristics assumed in the design. In addition, since the correction endoscope $11_{Ref}$ is used only in the case of the maintenance, for example, even when the correction endoscope is used for several years, a variation in the characteristic or degradation does not occur in the fluorescent substance $57_{Ref}$ due to the use thereof.

A color chart 90 integrated with the endoscope front end portion 35 is disposed in front of the illumination port 37.

Figure 8:
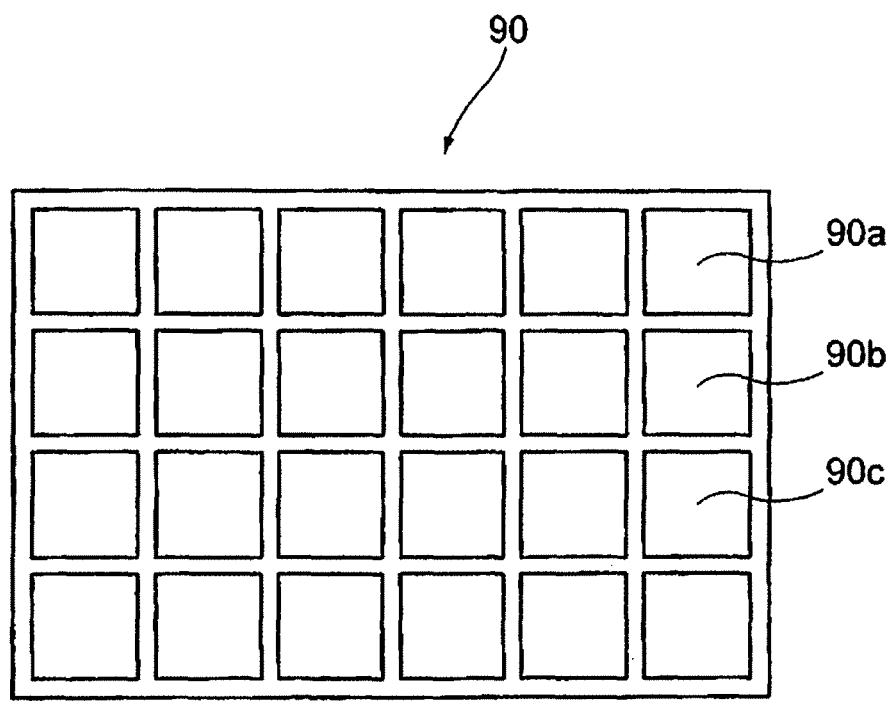
FIG. 8 is a front view showing a configuration example of a color chart.

The color chart 90 is disposed at a bottom surface of a cap 91 mounted to the endoscope front end portion 35, and the cap 91 is attachably/detachably mounted to the endoscope front end portion 35. For example, as shown in FIG. 8, the color chart 90 is formed by arranging a plurality of color patches 90a, 90b, 90c, and the like of reference colors having known tones on a plane.

As described above, the color chart 90 is disposed in front of the endoscope front end portion 35, the illumination light emitted from the illumination port 37 illuminates the color chart 90, and then the image of the illuminated color chart 90 is captured by an imaging element $21_{Ref}$ via an object lens unit $39_{Ref}$. Accordingly, the captured image signal output from the imaging element $21_{Ref}$ is input to an A/D converter $65_{Ref}$ via the scope cable 63, is converted into a digital signal, and then is output from the connector 25B. That is, in the correction endoscope $11_{Ref}$, the color chart 90 is illuminated by the fluorescent substance having a stipulated characteristic by supplying the laser light thereto, and the captured image signal of the captured color chart 90 is output.

Then, the processor 43 (refer to FIG. 1) of the control device 13 obtains the captured image signal of the color chart 90, and evaluates the characteristic of the blue laser light source on the basis of the captured image signal.

The captured image signal of the color chart 90 input to the processor 43 is obtained by the image capturing operation using the correction endoscope $11_{Ref}$, and the influence of a variation in the characteristic of the fluorescent substance 57 mounted to the endoscope 11 used for the actual endoscope examination may be ignored. For this reason, a variation in the characteristic of the blue laser light source 47 is obtained from a difference between the measured tones of the color patches 90a, 90b, 90c, and the like of the color chart 90 and the known tones (stipulated tones). In the present correction process, the tone correction table is rewritten so as to remove a difference between the measured tones and the known tones.

That is, the captured image signal of the color chart 90 photographed by the correction endoscope $11_{Ref}$ is used as an adjustment image, and the control section 67 determines a correction coefficient necessary for correcting the tones of the tone areas 90a, 90b, 90c, and the like of the adjustment image to be equal to the stipulated tones. The information of the determined correction coefficient is stored in the light source information storing section 74 of the control device 13.

After the above-described correction process is performed on the blue laser light source 47, when the correction endoscope $11_{Ref}$ is detached from the control device 13, and the normal endoscope 11 is connected to the control device 13, the information on the light emission characteristic of the fluorescent substance 57 of the endoscope 11 is read from the light emission characteristic storing section 75, and the contents of the tone correction table are rewritten on the basis of the light emission characteristic information of the fluorescent substance 57 and the correction coefficient representing the characteristic of the blue laser light source 47 stored in the light source information storing section 74. Accordingly, it is possible to remove the influence of a variation in the tone of the illumination light caused by a variation in the characteristic of the blue laser light source 47.

More specifically, when the control device 13 is connected to any one of the endoscopes 11, the control section 67 of the processor 43 obtains the light source characteristic information from the light source information storing section 74 of the light source device 41, and obtains the fluorescent substance light emission characteristic information as the excitation spectrum information and the light emission spectrum information from the light emission characteristic storing section 75 of the endoscope 11. Then, the control section 67 creates an illumination light spectral profile of the illumination light emitted from the front end of the endoscope 11 on the basis of the information of the original parameters. That is, the intensity of the fluorescent substance light emission spectrum is obtained from the light emission wavelength of the light source and the excitation spectrum of the fluorescent substance, and the spectral profile of the illumination light formed by synthesizing the fluorescent substance light emission spectrum with the blue laser light is obtained. In addition, the operation of obtaining the information from the light source information storing section 74 may be performed before the connection of the endoscope 11.

Subsequently, the control device 13 creates information necessary for correctly reproducing the tone in the corrected image on the basis of the contents of the illumination light spectral profile, and stores the information in the tone correction table 81. That is, in order to obtain the output image having a tone equivalent to that of the case of using the stipulated illumination light, the tone correction table 81 is created so as to subject the image signal to the correction of the tone corresponding to a difference between the stipulated spectral characteristic (profile) of the illumination light and the spectral characteristic of the actual illumination light. The contents of the tone correction table 81 are stored in the correction information storing section 72 shown in FIG. 1.

Then, the image processing section 73 of the control device 13 corrects the captured signal obtained from the endoscope 11 on the basis of the tone correction table 81 by referring to the correction information storing section 72, and outputs the observation image having the appropriate tone to the control section 67. By the above-described process, the image captured by the endoscope 11 is output to have an appropriate tone at all times regardless of the individual difference of the light source and the individual difference of the fluorescent substance of the endoscope, and is displayed or stored as an image having a tone appropriate for diagnosis.

Next, the modified example of the above-described endoscope system will be described hereinafter.

Figure 9:
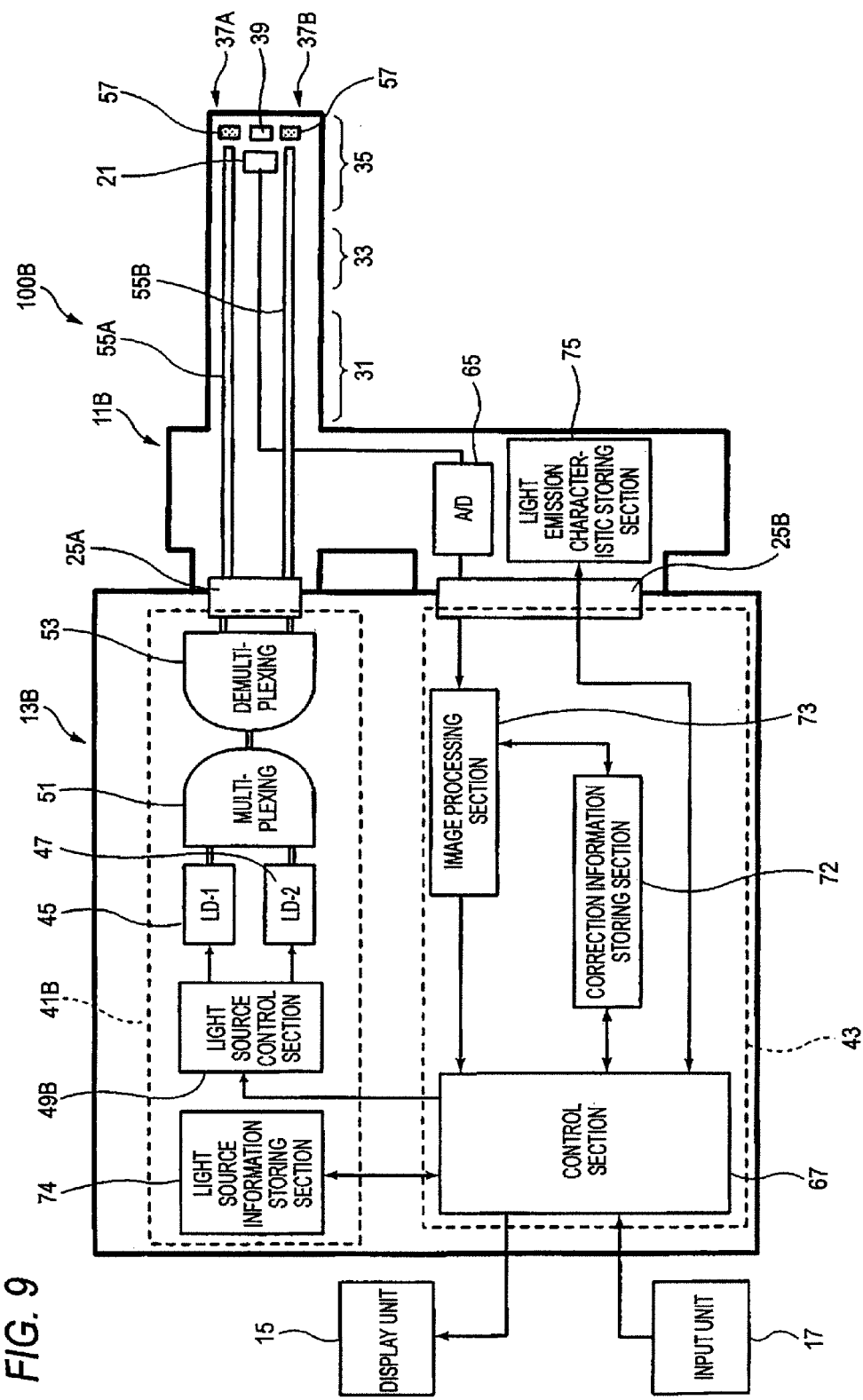
FIG. 9 is a block diagram showing a configuration of a modified example of the endoscope system shown in FIG. 1.

FIG. 9 shows the modified example of the endoscope system 100 shown in FIG. 1. In addition, the same reference numerals are given to the constituents shown in FIG. 9 and corresponding to those of FIG. 1. A light source device 41B of an endoscope system 100B shown in FIG. 9 includes a violet laser light source 45 in addition to the above-described blue laser light source 47 as the light source. The violet laser light source 45 is a laser diode which emits violet laser light having a central wavelength of 405 nm.

The light emitted from each of the semiconductor light emitting elements of the light sources 45 and 47 is individually controlled by a light source control section 49B, and the light amount ratio between the light emitted from the blue laser light source 47 and the light emitted from the violet laser light source 45 is changeable.

Then, the endoscope 11B is provided with two optical fibers 55A and 55B which are provided as two independent light guiding paths. Each of one ends of the optical fibers 55A and 55B is connected to the connector 25A, and each of the other ends extends to the front end portion 35 of the endoscope 11B. The front end portion 35 of the endoscope 11B is provided with two illumination ports 37A and 37B, and the fluorescent substance 57 is disposed in the inside of each of the illumination ports 37A and 37B. The laser light guided by the optical fiber 55A is supplied to the fluorescent substance 57A, and the laser light guided by the optical fiber 55B is supplied to the fluorescent substance 57B. Accordingly, in the endoscope system 100B shown in FIG. 9, any one or both of the white illumination light and the violet laser light are emitted from the two illumination ports 37A and 37B to the object.

According to the endoscope system 100B having the above-described configuration, it is possible to obtain the observation image illuminated by the light of the narrow bandwidth of wavelength generated by the violet laser light by accurately correcting the tone of the captured image in accordance with the tone of the white illumination light.

Figure 10:
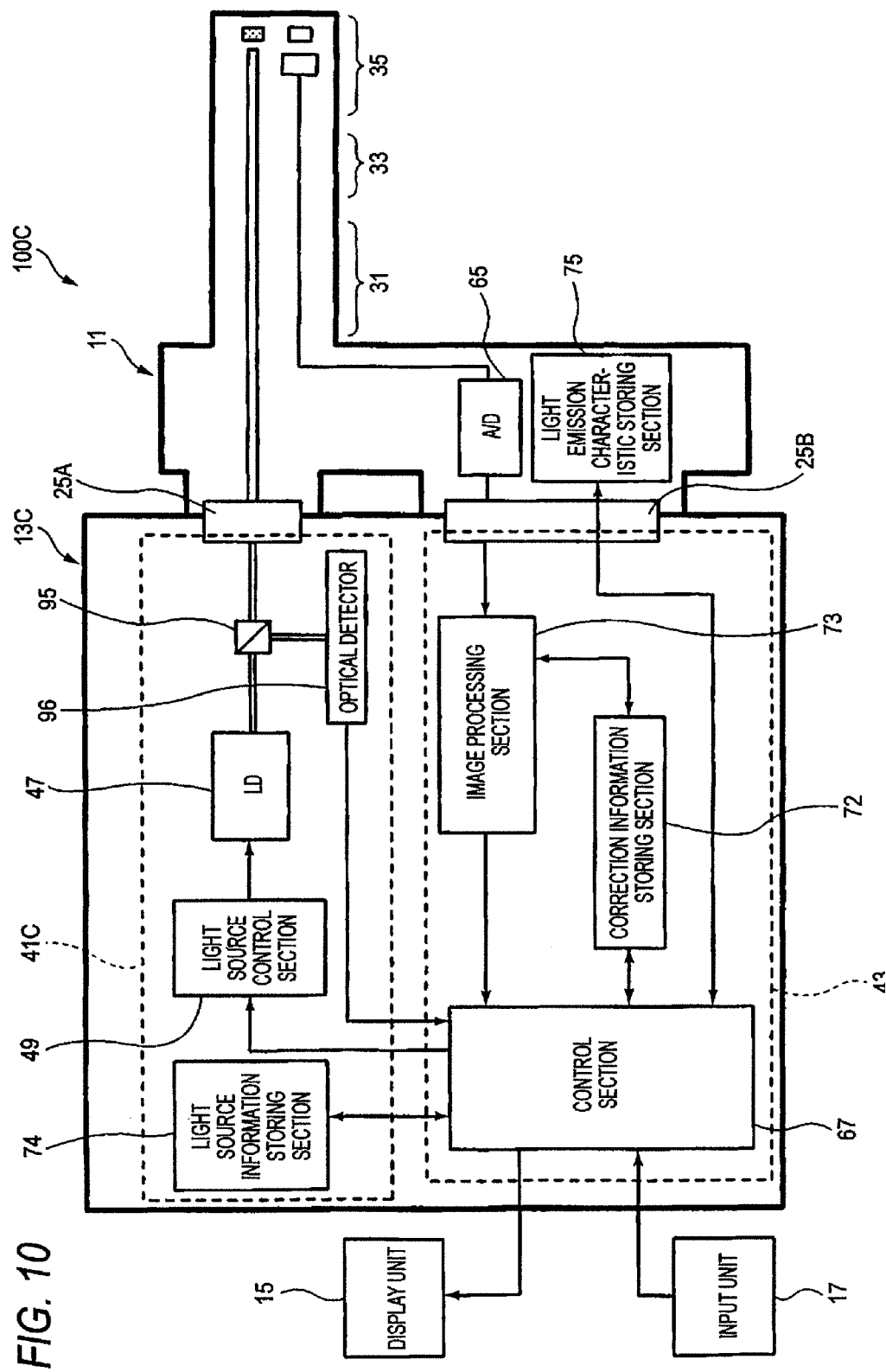
FIG. 10 is a block diagram showing another configuration example of the endoscope system shown in FIG. 1.

Next, another configuration example of the endoscope system is shown in FIG. 10. In addition, in FIG. 10, the same reference numerals are given to the constituents corresponding to those of FIG. 1. As shown in FIG. 10, an endoscope system 100C includes a dichroic mirror 95 and an optical detector 96 in the inside of a light source device 41C.

The dichroic mirror 95 is disposed in the course of the optical path from the optical output side of the blue laser light source 47 to the connector 25A, and guides a part of the blue laser light to the optical detector 96. The optical detector 96 has a function of detecting at least one of the central wavelength and the intensity of the input light, and desirably has a function of detecting both of them.

Accordingly, the processor 43 of the endoscope system 100C may obtain information on at least one of the actual wavelength and intensity of the blue laser light emitted from the blue laser light source 47 by the use of the optical detector 96. That is, in the case where the wavelength or the intensity of the laser light emitted from the blue laser light source 47 is changed, it is possible to directly detect the variation. For this reason, it is possible to perform the correction on the blue laser light source 47 without the use of the above-described correction endoscope $11_{Ref}$.

In addition, even in the endoscope system 100C, in the case of the configuration having a plurality of laser light sources as in the endoscope system 100B shown in FIG. 9, the light source device 41 may have a configuration in which the dichroic mirror is disposed in the course of the optical path between the combiner 51 and the coupler 53 of the light source device 41B shown in FIG. 9, and the light divided by the dichroic mirror is detected by the optical detector.

Figure 11:
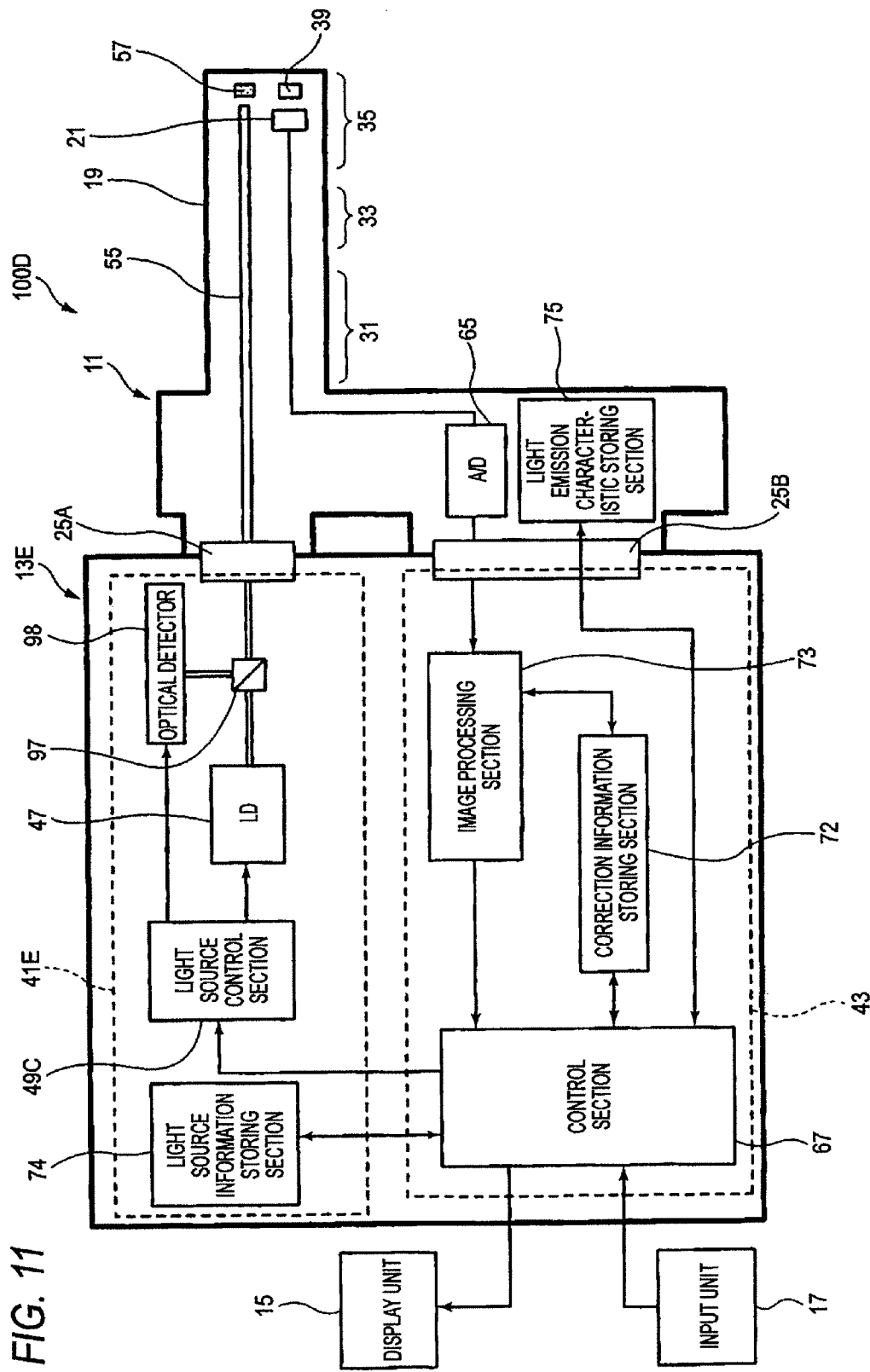
FIG. 11 is a block diagram showing another configuration example of the endoscope system shown in FIG. 1.

Next, another configuration example of the endoscope system is shown in FIG. 11. In addition, in FIG. 11, the same reference numerals are given to the constituents corresponding to those of FIG. 1. As shown in FIG. 11, an endoscope system 100D includes a dichroic mirror 97 and a correction reference light source 98 in the inside of a light source device 41E.

The dichroic mirror 97 guides each of the laser light output from the blue laser light source 47 and the laser light output from the correction reference light source 98 to the output connector 25A.

The correction reference light source 98 is a laser diode which emits blue laser light having a central wavelength of 445 nm as in the blue laser light source 47, and has a stipulated characteristic. That is, the wavelength of the laser light emitted from the correction reference light source 98 is adjusted so that an error with respect to the stipulated wavelength (445 nm) of the design becomes small. In addition, the output intensity of the laser light is adjusted so that an error with respect to the stipulated intensity characteristic of the design becomes small. Accordingly, it is possible to obtain the light source in which a difference in the characteristics is particularly adjusted to be small. Since the correction reference light source 98 is used only in the case of maintenance, the light source is not easily influenced by a variation over time, and may emit laser light having a stipulated characteristic for a long period of time.

A light source control section 49C exclusively controls the light emission of the blue laser light source 47 and the correction reference light source 98. That is, in a normal case, only the blue laser light source 47 is controlled to be turned on, and the correction reference light source 98 is maintained to be turned off. In the case of maintenance, the correction reference light source 98 is controlled to be turned on while maintaining the blue laser light source 47 to be turned off, or the blue laser light source 47 and the correction reference light source 98 are alternately turned on.

In the case of the endoscope system 100D, even in the case where a variation occurs in the characteristic of the blue laser light source 47, it is possible to supply to the endoscope 11 the blue laser light having a stipulated characteristic by using the correction reference light source 98. For this reason, it is possible to simply correct the light emission characteristic of the fluorescent substance 57 of the endoscope 11.

In the case where the characteristic of the fluorescent substance 57 of the endoscope 11 is corrected, the blue laser light source 47 is turned off, and the correction reference light source 98 is turned on while the endoscope 11 is connected to a control device 13E as shown in FIG. 11, thereby supplying the blue laser light emitted to the correction reference light source 98 to the endoscope 11. In addition, although not shown in the drawings, the illumination light of the endoscope 11 is emitted to the above-described color chart, and the image of the color chart is captured by the imaging element 21. The processor 43 uses the captured image signal, output from the imaging element 21 capturing the image of the color chart when the correction reference light source 98 is turned on, as the adjustment image in the same manner as described above. Accordingly, it is possible to correct a variation in the tone of the captured image or a variation in the tone of the illumination light based on a variation in the characteristic of the fluorescent substance 57.

In addition, in the endoscope system 100D, in the case of the configuration having a plurality of laser light sources as in the endoscope system 100B shown in FIG. 9, the light source device 41 may have a configuration in which the dichroic mirror is disposed in the course of the optical path between the combiner 51 and the coupler 53 of the light source device 41B shown in FIG. 9, and the correction reference light source 98 is disposed on the optical path divided by the dichroic mirror.

The present invention is not limited to the above-described embodiment, but corrections and applications thereof may be made by the person skilled in the art on the basis of the description of the specification and the known technology, and those are included in the scope requiring protection.

As described above, the present specification discloses the following items.

(1) An endoscope system including an endoscope which includes an illumination optical system having a fluorescent substance and an imaging optical system having an imaging element; and a control device which is connected to the endoscope, the control device including a light source unit having a semiconductor light emitting element generating excitation light used to excite the fluorescent substance, a storage section storing predetermined color correction information, and an image processing section creating captured image data by performing a calculation process on an image signal output from the imaging element on the basis of the color correction information, the endoscope system including: an optical characteristic detecting means for detecting at least one of optical characteristics of the fluorescent substance and the semiconductor light emitting element; and a color correction information correcting means for correcting the color correction information stored in the storage section on the basis of the optical characteristic detected by the optical characteristic detecting means.

According to the endoscope system, in the case of using the endoscope including the illumination optical system having the laser light source and the fluorescent substance and the imaging optical system having the imaging element, it is possible to simplify a mantenance operation performed by a user to correct the color correction information in the event of a variation in tone of the captured image caused by a variation over time or the like. Accordingly, it is possible to accurately perform the color correction on the captured image of the endoscope at all times, and to reliably maintain the diagnosis precision of the endoscope with high precision.

(2) The endoscope system according to (1), further including: a correction endoscope which is connectable to the control device instead of the endoscope, and includes an illumination optical system having a correction reference fluorescent substance with a stipulated light emission characteristic and an imaging optical system having an imaging element; and a color chart which includes a plurality of color patches each having a known tone, wherein the optical characteristic detecting means obtains chromaticity information involved with each chromacity of a plurality of chromacity areas on the basis of an adjustment image signal output from the imaging element inside the correction endoscope when capturing the image of the color chart while the correction endoscope is connected to the control device, and calculates corrected color correction information necessary for the correction of the color correction information by the use of the chromacity information, and wherein the color correction information correcting means corrects the color correction information stored in the storage section on the basis of the corrected color correction information.

According to the endoscope system, since the captured image of the color chart photographed by using the correction endoscope is not influenced by a variation in the characteristic of the fluorescent substance of the endoscope, it is possible to highly precisely detect a variation in the characteristic of the semiconductor light emitting element of the light source unit, and to change the color correction information of the storage section so as to correct a variation in the characteristic.

(3) The endoscope system according to (2), wherein the color chart is integrated with the correction endoscope.

According to the endoscope system, since the color chart used for the correction is integrated with the correction endoscope, it is not necessary to perform the operation of installing or positioning the color chart, and thus the convenience is improved.

(4) The endoscope system according to (1), wherein the optical characteristic detecting means includes a wavelength detector which detects a light emission wavelength of the semiconductor light emitting element, and wherein the color correction information correcting means corrects the color correction information on the basis of a stipulated value of the light emission wavelength of the semiconductor light emitting element and a measured value of the light emission wavelength of the semiconductor light emitting element detected by the wavelength detector.

According to the endoscope system, even in the case where the light emission wavelength of the semiconductor light emitting element is changed, it is possible to change the color correction information so as to remove the influence of the variation. That is, since the spectrum of the illumination light having an influence on the chromacity of the output image is determined in accordance with the excitation spectrum, the light emission spectrum, or the like representing the absorption characteristic of the fluorescent substance, it is possible to estimate a variation in the spectrum of the illumination light on the basis of the stipulated value (a value before a variation) and the measured value (a current value) of the light emission wavelength of the semiconductor light emitting element, and to correctly correct the color correction information in consideration of the variation.

(5) The endoscope system according to (1), wherein the optical characteristic detecting means includes a light emission intensity detector which detects light emission intensity of the semiconductor light emitting element, and wherein the color correction information correcting means corrects the color correction information on the basis of a difference between a stipulated value of the light emission intensity of the semiconductor light emitting element and a measured value of the light emission intensity of the semiconductor light emitting element detected by the light emission intensity detector.

According to the endoscope system, even when the light emission intensity of the semiconductor light emitting element is changed in accordance with a variation over time, it is possible to change the information of the color correction information so as to remove the influence of the variation. That is, since the spectrum of the illumination light having an influence on the chromacity of the output image is influenced by the balance of the intensity of the light obtained by exciting the fluorescent substance to emit light, and the wavelength and the intensity of the light component emitted from the light source and used as the illumination light, it is possible to estimate a variation in the spectrum of the illumination light on the basis of the stipulated value (a value before a variation) and the measured value (a current value) of the light emission intensity of the semiconductor light emitting element, and to correctly correct the chromacity correction information in consideration of the variation.

(6) The endoscope system according to (1), further including: a correction semiconductor light emitting element which is controlled to be turned on at an exclusive timing different from that of the semiconductor light emitting element of the light source unit, and emits light in accordance with a stipulated wavelength; and a color chart which includes a plurality of color patches each having known chromacity, wherein the optical characteristic detecting means obtains chromacity information involved with each chromacity of a plurality of chromacity areas on the basis of an adjustment image signal obtained by emitting illumination light, obtained by supplying the light generated from the correction semiconductor light emitting element to the illumination optical system, to the color chart, and capturing the image of the color chart by using the imaging element while the endoscope is connected to the control device, and calculates corrected color correction information necessary for the correction of the color correction information by using the obtained chromacity information, and wherein the color correction information correcting means corrects the color correction information stored in the storage section on the basis of the corrected color correction information.

According to the endoscope system, it is possible to use the correction semiconductor light emitting element as the light source, and to use the color chart as the object during the correction operation. For this reason, even when the characteristic of the semiconductor light emitting element is changed due to a variation over time, it is possible to perform the correction operation without the influence of the variation. That is, since the chromacity information is obtained by capturing the image of the color chart using the illumination light obtained by using the fluorescent substance of the illumination optical system and the light emitted from the correction semiconductor light emitting element, it is possible to correct the color correction information so as to remove a variation in the characteristics of the fluorescent substance.

(7) The endoscope system according to (1), wherein the light source unit includes a plurality of semiconductor light emitting elements, and a multiplexer means for multiplexing the lights output from the respective semiconductor light emitting elements, and supplies the light multiplexed by the multiplexer means to the illumination optical system.

According to the endoscope system, it is possible to create the illumination light having a more appropriate tone by using, for example, a plurality of semiconductor light emitting elements generating lights having different wavelengths.

(8) The endoscope system according to (7), further including: a demultiplexer means for demultiplexing the light multiplexed by the multiplexer means, and supplying the demultiplexed lights to a plurality of light guiding paths, wherein the fluorescent substance of the illumination optical system is disposed at each of a plurality of positions of a front end of an insertion unit of the endoscope inserted into a body cavity, and wherein the lights output from the demultiplexer means are respectively supplied to the fluorescent substances of the plurality of positions via the plurality of light guiding paths.

According to the endoscope system, since it is possible to illuminate the object by emitting the illumination light from the plurality of positions of the front end of the insertion unit of the endoscope, it is possible to illuminate a wide area with uniform illumination intensity without any occurrence of irregularities.

What is claimed is:

1. An endoscope system including an endoscope which includes an illumination optical system having a fluorescent substance and an imaging optical system having an imaging element; and a control device which is connected to the endoscope, the control device including a light source unit having a semiconductor light emitting element generating excitation light used to excite the fluorescent substance, a storage section storing predetermined color correction information, and an image processing section creating captured image data by performing a calculation process on an image signal output from the imaging element on the basis of the color correction information, the endoscope system comprising:
   an optical characteristic detecting unit for detecting at least one of optical characteristics of the fluorescent substance and the semiconductor light emitting element; and
   a color correction information correcting unit for correcting the color correction information stored in the storage section on the basis of the optical characteristic detected by the optical characteristic detecting unit,
   wherein the optical characteristic detecting unit includes a light emission intensity detector which detects light emission intensity of the semiconductor light emitting element,
   wherein the color correction information correcting unit corrects the color correction information on the basis of a difference between a stipulated value of the light emission intensity of the semiconductor light emitting element and a measured value of the light emission intensity of the semiconductor light emitting element detected by the light emission intensity detector, and
   wherein, in a case where the endoscope connected to the control device is exchanged, the color correction information is newly created in accordance with at least one of optical characteristics of the fluorescent substance and the semiconductor light emitting element of the endoscope which is connected after the exchange, and the color correction information is updated.

2. The endoscope system according to claim 1, further comprising:
   a correction endoscope which is connectable to the control device instead of the endoscope, and includes an illumination optical system having a correction reference fluorescent substance with a stipulated light emission characteristic and an imaging optical system having an imaging element; and
   a color chart which includes a plurality of color patches each having a known chromacity,
   wherein the optical characteristic detecting unit obtains chromacity information relating to each chromacity of a plurality of chromacity areas on the basis of an adjustment image signal output from the imaging element inside the correction endoscope when capturing the image of the color chart while the correction endoscope is connected to the control device, and calculates corrected color correction information necessary for the correction of the color correction information by the use of the chromacity information, and
   wherein the color correction information correcting unit corrects the color correction information stored in the storage section on the basis of the corrected color correction information.

3. The endoscope system according to claim 2,
   wherein the color chart is integrated with the correction endoscope.

4. The endoscope system according to claim 1,
   wherein the optical characteristic detecting unit includes a wavelength detector which detects a light emission wavelength of the semiconductor light emitting element, and
   wherein the color correction information correcting unit corrects the color correction information on the basis of a stipulated value of the light emission wavelength of the semiconductor light emitting element and a measured value of the light emission wavelength of the semiconductor light emitting element detected by the wavelength detector.

5. The endoscope system according to claim 1, further comprising:
   a correction semiconductor light emitting element which is controlled to be turned on at an exclusive timing different from that of the semiconductor light emitting element of the light source unit, and emits light in accordance with a stipulated wavelength; and
   a color chart which includes a plurality of color patches each having known chromacity,
   wherein the optical characteristic detecting unit obtains chromacity information relating to each chromacity of a plurality of chromacity areas on the basis of an adjustment image signal obtained by emitting illumination light, obtained by supplying the light generated from the correction semiconductor light emitting element to the illumination optical system, to the color chart, and capturing the image of the color chart by using the imaging element while the endoscope is connected to the control device, and calculates corrected color correction information necessary for the correction of the color correction information by using the obtained chromacity information, and
   wherein the color correction information correcting unit corrects the color correction information stored in the storage section on the basis of the corrected color correction information.

6. The endoscope system according to claim 1,
   wherein the light source unit includes a plurality of semiconductor light emitting elements, and a multiplexer unit for multiplexing the lights output from the respective semiconductor light emitting elements, and supplies the light multiplexed by the multiplexer unit to the illumination optical system.

7. The endoscope system according to claim 6, further comprising:
- a demultiplexer unit for demultiplexing the light multiplexed by the multiplexer unit, and supplying the demultiplexed lights to a plurality of light guiding paths,
- wherein the fluorescent substance of the illumination optical system is disposed at each of a plurality of positions of a front end of an insertion unit of the endoscope inserted into a body cavity, and
- wherein the lights output from the demultiplexer unit are respectively supplied to the fluorescent substances of the plurality of positions via the plurality of light guiding paths.

8. The endoscope system according to claim 1, wherein the control device is configured to determine a correction coefficient for correcting the color correction information, and the correction coefficient is stored in the storage section.

* * * * *